(12) United States Patent
Oh et al.

(10) Patent No.: US 6,770,750 B2
(45) Date of Patent: Aug. 3, 2004

(54) SMALL AND CYSTEINE RICH ANTIFUNGAL DEFENSIN AND THIONIN-LIKE PROTEIN GENES HIGHLY EXPRESSED IN THE INCOMPATIBLE INTERACTION

(75) Inventors: Boung-Jun Oh, Kwangju (KR); Moon Kyung Ko, Kwangju (KR); Byongchul Shin, Kwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 228 days.

(21) Appl. No.: 09/854,562

(22) Filed: May 15, 2001

(65) Prior Publication Data

US 2003/0096985 A1 May 22, 2003

Related U.S. Application Data

(62) Division of application No. 09/442,631, filed on Nov. 18, 1999, now Pat. No. 6,300,489.

(51) Int. Cl.[7] ............................................. C07H 19/04
(52) U.S. Cl. ....................................................... 536/23.6
(58) Field of Search ............................. 536/23.6, 23.1; 435/69.1, 172.3, 252.3, 320.1; 530/350

(56) References Cited

U.S. PATENT DOCUMENTS

| | | | |
|---|---|---|---|
| 5,608,144 A | | 3/1997 | Baden et al. ................ 800/205 |
| 5,719,043 A | * | 2/1998 | Frommer .................... 435/69.1 |

OTHER PUBLICATIONS

Oh et al., *Coexpression of a defensin gene and thionin-like gene via differential signal transduction pathways in pepper and colletotrichum gloeosporiodes interactions*, Plant Molecular Biology, 1999, 41(3):313–319.

Epple et al., *An Arabidopsis thaliana Thionin Gene Is Inducible via a Signal Transduction Pathway Different from That for Patogenesis–Related Proteins*, Plant Physiol., 1995, 109:813–820.

Terras et al., *Small Cysteine–Rich Antifungal Proteins from Radish: Their Role in Host Defense*, The Plant Cell, 1995, 7:573–588.

Heck & Ho, *Gibberellin–repressible gene expression in the barley aleurone layer*, Plant Molecular Biology, 1996, 30:611–623.

Ebrahim–Nesbat et al., *Cultivar–related differences in the distribution of cell–wall–bound thionins in compatible and incompatible interactions between barley and powdery mildew*, Planta, 1989, 179:203–210.

Penninckx et al., *Pathogen–Induced Systemic Activation of a Plant Defensin Gene in Arabidopsis Follows a Salicylic Acid–Independent Pathway*, The Plant Cell, 1996, 8:2309–2323.

Salzman et al., *Coordinate Accumulation of Antifungal Proteins and Hexoses Constitutes a Developmentally Controlled Defense Response during Fruit Ripening in Grape*, Plant Physiol., 1998, 117:465–472.

Manandhar et al., *Anthraenose Development on Pepper Fruits Inoculated with coletotrichum gloeosporioides*, Plant Disease, 1995, 79(4):380–383.

Bohlmann et al., *Leaf–specific thionins of barley—a novel class of cell wall proteins toxic to plant–pathogenic fungi and possibly involved in the defence mechanism of plants*, The EMBO Journal, 1988, 7(6):1559–1565.

\* cited by examiner

*Primary Examiner*—Karen Cochrane Carlson
*Assistant Examiner*—Sheridan K Snedden
(74) *Attorney, Agent, or Firm*—Kenyon & Kenyon

(57) ABSTRACT

The present invention related to two cDNA clones, designated to PepDef (pepper defensin protein gene) and PepThi (pepper thionin-like protein gene) and individual component; thereof including its coding region and its gene product; modification thereto; application of said gene, coding region and modification thereto; DNA construct, vectors and transformed plants each comprising the gene or part thereof.

1 Claim, 4 Drawing Sheets

FIG. 1

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1685 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Arabidopsis thaliano (ix) FEATURE:
      (A) NAME/KEY: CDS
      (B) LOCATION: 57..1511
      (D) OTHER INFORMATION: /note= "amino acid transporter"

(xi) SEQUENCE DESCRIPTION: SEQ ID NO: 1:

```
CTTAAAACAT TTATTTTATC TTCTTCTTGT TCTCTCTTTC TCTTTCTCTC ATCACT            56

ATG AAG AGT TTC AAC ACA GAA GGA CAC AAC CAC TCC ACG GCG GAA TCC        104
Met Lys Ser Phe Asn Thr Glu Gly His Asn His Ser Thr Ala Glu Ser
  1               5                  10                  15

GGC GAT GCC TAC ACC GTG TCG GAC CCG ACA AAG AAC GTC GAT GAA GAT        152
Gly Asp Ala Tyr Thr Val Ser Asp Pro Thr Lys Asn Val Asp Glu Asp
             20                  25                  30

GGT CGA GAG AAG CGT ACC GGG ACG TGG CTT ACG GCG AGT GCG CAT ATT        200
Gly Arg Glu Lys Arg Thr Gly Thr Trp Leu Thr Ala Ser Ala His Ile
         35                  40                  45

ATC ACG GCG GTG ATA GGC TCC GGA GTG TTG TCT TTA GCA TGG GCT ATA        248
Ile Thr Ala Val Ile Gly Ser Gly Val Leu Ser Leu Ala Trp Ala Ile
     50                  55                  60

GCT CAG CTT GGT TGG ATC GCA GGG ACA TCG ATC TTA CTC ATT TTC TCG        296
Ala Gln Leu Gly Trp Ile Ala Gly Thr Ser Ile Leu Leu Ile Phe Ser
 65                  70                  75                  80

TTC ATT ACT TAC TTC ACC TCC ACC ATG CTT GCC GAT TGC TAC CGT GCG        344
Phe Ile Thr Tyr Phe Thr Ser Thr Met Leu Ala Asp Cys Tyr Arg Ala
                 85                  90                  95

CCG GAT CCC GTC ACC GGA AAA CGG AAT TAC ACT TAC ATG GAC GTT GTT        392
Pro Asp Pro Val Thr Gly Lys Arg Asn Tyr Thr Tyr Met Asp Val Val
            100                 105                 110

CGA TCT TAC CTC GGT GGT AGG AAA GTG CAG CTC TGT GGA GTG GCA CAA        440
```

-continued

```
                    Arg Ser Tyr Leu Gly Gly Arg Lys Val Gln Leu Cys Gly Val Ala Gln
                                115                 120                 125

TAT GGG AAT CTG ATT GGG GTC ACT GTT GGT TAC ACC ATC ACT GCT TCT          488
Tyr Gly Asn Leu Ile Gly Val Thr Val Gly Tyr Thr Ile Thr Ala Ser
        130                 135                 140

ATT AGT TTG GTA GCG GTA GGG AAA TCG AAC TGC TTC CAC GAT AAA GGG          536
Ile Ser Leu Val Ala Val Gly Lys Ser Asn Cys Phe His Asp Lys Gly
145                 150                 155                 160

CAC ACT GCG GAT TGT ACT ATA TCG AAT TAT CCG TAT ATG GCG GTT TTT          584
His Thr Ala Asp Cys Thr Ile Ser Asn Tyr Pro Tyr Met Ala Val Phe
                    165                 170                 175

GGT ATC ATT CAA GTT ATT CTT AGC CAG ATC CCA AAT TTC CAC AAG CTC          632
Gly Ile Ile Gln Val Ile Leu Ser Gln Ile Pro Asn Phe His Lys Leu
                180                 185                 190

TCT TTT CTT TCC ATT ATG GCC GCA GTC ATG TCC TTT ACT TAT GCA ACT          680
Ser Phe Leu Ser Ile Met Ala Ala Val Met Ser Phe Thr Tyr Ala Thr
            195                 200                 205

ATT GGA ATC GGT CTA GCC ATC GCA ACC GTC GCA GGT GGG AAA GTG GGT          728
Ile Gly Ile Gly Leu Ala Ile Ala Thr Val Ala Gly Gly Lys Val Gly
        210                 215                 220

AAG ACG AGT ATG ACG GGC ACA GCG GTT GGA GTA GAT GTA ACC GCA GCT          776
Lys Thr Ser Met Thr Gly Thr Ala Val Gly Val Asp Val Thr Ala Ala
225                 230                 235                 240

CAA AAG ATA TGG AGA TCG TTT CAA GCG GTT GGG GAC ATA GCG TTC GCC          824
Gln Lys Ile Trp Arg Ser Phe Gln Ala Val Gly Asp Ile Ala Phe Ala
                    245                 250                 255

TAT GCT TAT GCC ACG GTT CTC ATC GAG ATT CAG GAT ACA CTA AGA TCT          872
Tyr Ala Tyr Ala Thr Val Leu Ile Glu Ile Gln Asp Thr Leu Arg Ser
                260                 265                 270

AGC CCA GCT GAG AAC AAA GCC ATG AAA AGA GCA AGT CTT GTG GGA GTA          920
Ser Pro Ala Glu Asn Lys Ala Met Lys Arg Ala Ser Leu Val Gly Val
            275                 280                 285

TCA ACC ACC ACT TTT TTC TAC ATC TTA TGT GGA TGC ATC GGC TAT GCT          968
Ser Thr Thr Thr Phe Phe Tyr Ile Leu Cys Gly Cys Ile Gly Tyr Ala
        290                 295                 300

GCA TTT GGA AAC AAT GCC CCT GGA GAT TTC CTC ACA GAT TTC GGG TTT         1016
Ala Phe Gly Asn Asn Ala Pro Gly Asp Phe Leu Thr Asp Phe Gly Phe
305                 310                 315                 320

TTC GAG CCC TTT TGG CTC ATT GAC TTT GCA AAC GCT TGC ATC GCT GTC         1064
Phe Glu Pro Phe Trp Leu Ile Asp Phe Ala Asn Ala Cys Ile Ala Val
                    325                 330                 335

CAC CTT ATT GGT GCC TAT CAG GTG TTC GCG CAG CCG ATA TTC CAG TTT         1112
His Leu Ile Gly Ala Tyr Gln Val Phe Ala Gln Pro Ile Phe Gln Phe
                340                 345                 350

GTT GAG AAA AAA TGC AAC AGA AAC TAT CCA GAC AAC AAG TTC ATC ACT         1160
Val Glu Lys Lys Cys Asn Arg Asn Tyr Pro Asp Asn Lys Phe Ile Thr
            355                 360                 365

TCT GAA TAT TCA GTA AAC GTA CCT TTC CTT GGA AAA TTC AAC ATT AGC         1208
Ser Glu Tyr Ser Val Asn Val Pro Phe Leu Gly Lys Phe Asn Ile Ser
        370                 375                 380

CTC TTC AGA TTG GTG TGG AGG ACA GCT TAT GTG GTT ATA ACC ACT GTT         1256
Leu Phe Arg Leu Val Trp Arg Thr Ala Tyr Val Val Ile Thr Thr Val
385                 390                 395                 400

GTA GCT ATG ATA TTC CCT TTC TTC AAC GCG ATC TTA GGT CTT ATC GGA         1304
Val Ala Met Ile Phe Pro Phe Phe Asn Ala Ile Leu Gly Leu Ile Gly
                    405                 410                 415

GCA GCT TCC TTC TGG CCT TTA ACG GTT TAT TTC CCT GTG GAG ATG CAC         1352
Ala Ala Ser Phe Trp Pro Leu Thr Val Tyr Phe Pro Val Glu Met His
                420                 425                 430
```

-continued

```
ATT GCA CAA ACC AAG ATT AAG AAG TAC TCT GCT AGA TGG ATT GCG CTG      1400
Ile Ala Gln Thr Lys Ile Lys Lys Tyr Ser Ala Arg Trp Ile Ala Leu
            435                 440                 445

AAA ACG ATG TGC TAT GTT TGC TTG ATC GTC TCG CTC TTA GCT GCA GCC      1448
Lys Thr Met Cys Tyr Val Cys Leu Ile Val Ser Leu Leu Ala Ala Ala
450                 455                 460

GGA TCC ATC GCA GGA CTT ATA AGT AGT GTC AAA ACC TAC AAG CCC TTC      1496
Gly Ser Ile Ala Gly Leu Ile Ser Ser Val Lys Thr Tyr Lys Pro Phe
465                 470                 475                 480

CGG ACT ATG CAT GAG TGAGTTTGAG ATCCTCAAGA GAGTCAAAAA TATATGTAGT      1551
Arg Thr Met His Glu
                485

AGTTTGGTCT TTCTGTTAAA CTATCTGGTG TCTAAATCCA ATGAGAATGC TTTATTGC      1611

AAACTTCATG AATCTCTCTG TATCTACATC TTTCAATCTA ATACATATGA GCTCTTCC      1671

AAAAAAAAAA AAAA                                                      1685
```

(2) INFORMATION FOR SEQ ID NO: 2:

(i) SEQUENCE CHARACTERISTICS:
        (A) LENGTH: 485 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Ser Phe Asn Thr Glu Gly His Asn His Ser Thr Ala Glu Ser
1               5                   10                  15

Gly Asp Ala Tyr Thr Val Ser Asp Pro Thr Lys Asn Val Asp Glu Asp
                20                  25                  30

Gly Arg Glu Lys Arg Thr Gly Thr Trp Leu Thr Ala Ser Ala His Ile
            35                  40                  45

Ile Thr Ala Val Ile Gly Ser Gly Val Leu Ser Leu Ala Trp Ala Ile
        50                  55                  60

Ala Gln Leu Gly Trp Ile Ala Gly Thr Ser Ile Leu Leu Ile Phe Ser
65                  70                  75                  80

Phe Ile Thr Tyr Phe Thr Ser Thr Met Leu Ala Asp Cys Tyr Arg Ala
                85                  90                  95

Pro Asp Pro Val Thr Gly Lys Arg Asn Tyr Thr Tyr Met Asp Val Val
                100                 105                 110

Arg Ser Tyr Leu Gly Gly Arg Lys Val Gln Leu Cys Gly Val Ala Gln
            115                 120                 125

Tyr Gly Asn Leu Ile Gly Val Thr Val Gly Tyr Thr Ile Thr Ala Ser
130                 135                 140

Ile Ser Leu Val Ala Val Gly Lys Ser Asn Cys Phe His Asp Lys Gly
145                 150                 155                 160

His Thr Ala Asp Cys Thr Ile Ser Asn Tyr Pro Tyr Met Ala Val Phe
                165                 170                 175

Gly Ile Ile Gln Val Ile Leu Ser Gln Ile Pro Asn Phe His Lys Leu
            180                 185                 190

Ser Phe Leu Ser Ile Met Ala Ala Val Met Ser Phe Thr Tyr Ala Thr
        195                 200                 205

Ile Gly Ile Gly Leu Ala Ile Ala Thr Val Ala Gly Lys Val Gly
        210                 215                 220

Lys Thr Ser Met Thr Gly Thr Ala Val Gly Val Asp Val Thr Ala Ala
225                 230                 235                 240
```

-continued

```
Gln Lys Ile Trp Arg Ser Phe Gln Ala Val Gly Asp Ile Ala Phe Ala
                245                 250                 255

Tyr Ala Tyr Ala Thr Val Leu Ile Glu Ile Gln Asp Thr Leu Arg Ser
            260                 265                 270

Ser Pro Ala Glu Asn Lys Ala Met Lys Arg Ala Ser Leu Val Gly Val
        275                 280                 285

Ser Thr Thr Thr Phe Phe Tyr Ile Leu Cys Gly Cys Ile Gly Tyr Ala
    290                 295                 300

Ala Phe Gly Asn Asn Ala Pro Gly Asp Phe Leu Thr Asp Phe Gly Phe
305                 310                 315                 320

Phe Glu Pro Phe Trp Leu Ile Asp Phe Ala Asn Ala Cys Ile Ala Val
                325                 330                 335

His Leu Ile Gly Ala Tyr Gln Val Phe Ala Gln Pro Ile Phe Gln Phe
            340                 345                 350

Val Glu Lys Lys Cys Asn Arg Asn Tyr Pro Asp Asn Lys Phe Ile Thr
        355                 360                 365

Ser Glu Tyr Ser Val Asn Val Pro Phe Leu Gly Lys Phe Asn Ile Ser
    370                 375                 380

Leu Phe Arg Leu Val Trp Arg Thr Ala Tyr Val Val Ile Thr Thr Val
385                 390                 395                 400

Val Ala Met Ile Phe Pro Phe Phe Asn Ala Ile Leu Gly Leu Ile Gly
                405                 410                 415

Ala Ala Ser Phe Trp Pro Leu Thr Val Tyr Phe Pro Val Glu Met His
            420                 425                 430

Ile Ala Gln Thr Lys Ile Lys Lys Tyr Ser Ala Arg Trp Ile Ala Leu
        435                 440                 445

Lys Thr Met Cys Tyr Val Cys Leu Ile Val Ser Leu Leu Ala Ala Ala
    450                 455                 460

Gly Ser Ile Ala Gly Leu Ile Ser Ser Val Lys Thr Tyr Lys Pro Phe
465                 470                 475                 480

Arg Thr Met His Glu
                485
```

(2) INFORMATION FOR SEQ ID NO: 3:

(i) SEQUENCE CHARACTERISTICS:
        (A) LENGTH: 1740 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Arabidopsis thaliana (ix) FEATURE:
        (A) NAME/KEY: CDS
        (B) LOCATION: 80..1558
        (D) OTHER INFORMATION: /product= "amino acid transporter"

(xi) SEQUENCE DESCRIPTION: SEQ ID NO: 3:

```
CTATTTTATA ATTCCTCTTC TTTTTGTTCA TAGCTTTGTA ATTATAGTCT TATTTCTCTT      60

TAAGGCTCAA TAAGAGGAG ATG GGT GAA ACC GCT GCC GCC AAT AAC CAC CGT     112
                    Met Gly Glu Thr Ala Ala Ala Asn Asn His Arg
                      1               5                  10

CAC CAC CAC CAT CAC GGC CAC CAG GTC TTT GAC GTG GCC AGC CAC GAT     160
His His His His His Gly His Gln Val Phe Asp Val Ala Ser His Asp
             15                  20                  25
```

-continued

| | | |
|---|---|---|
| TTC GTC CCT CCA CAA CCG GCT TTT AAA TGC TTC GAT GAT GAT GGC CGC<br>Phe Val Pro Pro Gln Pro Ala Phe Lys Cys Phe Asp Asp Asp Gly Arg<br>30     35     40 | 208 |
| CTC AAA AGA ACT GGG ACT GTT TGG ACC GCG AGC GCT CAT ATA ATA ACT<br>Leu Lys Arg Thr Gly Thr Val Trp Thr Ala Ser Ala His Ile Ile Thr<br>45     50     55 | 256 |
| GCG GTT ATC GGA TCC GGC GTT TTG TCA TTG GCG TGG GCG ATT GCA CAG<br>Ala Val Ile Gly Ser Gly Val Leu Ser Leu Ala Trp Ala Ile Ala Gln<br>60     65     70     75 | 304 |
| CTC GGA TGG ATC GCT GGC CCT GCT GTG ATG CTA TTG TTC TCT CTT GTT<br>Leu Gly Trp Ile Ala Gly Pro Ala Val Met Leu Leu Phe Ser Leu Val<br>    80     85     90 | 352 |
| ACT CTT TAC TCC TCC ACA CTT CTT AGC GAC TGC TAC AGA ACC GGC GAT<br>Thr Leu Tyr Ser Ser Thr Leu Leu Ser Asp Cys Tyr Arg Thr Gly Asp<br>    95     100     105 | 400 |
| GCA GTG TCT GGC AAG AGA AAC TAC ACT TAC ATG GAT GCC GTT CGA TCA<br>Ala Val Ser Gly Lys Arg Asn Tyr Thr Tyr Met Asp Ala Val Arg Ser<br>    110     115     120 | 448 |
| ATT CTC GGT GGG TTC AAG TTC AAG ATT TGT GGG TTG ATT CAA TAC TTG<br>Ile Leu Gly Gly Phe Lys Phe Lys Ile Cys Gly Leu Ile Gln Tyr Leu<br>125     130     135 | 496 |
| AAT CTC TTT GGT ATC GCA ATT GGA TAC ACG ATA GCA GCT TCC ATA AGC<br>Asn Leu Phe Gly Ile Ala Ile Gly Tyr Thr Ile Ala Ala Ser Ile Ser<br>140     145     150     155 | 544 |
| ATG ATG GCG ATC AAG AGA TCC AAC TGC TTC CAC AAG AGT GGA GGA AAA<br>Met Met Ala Ile Lys Arg Ser Asn Cys Phe His Lys Ser Gly Gly Lys<br>    160     165     170 | 592 |
| GAC CCA TGT CAC ATG TCC AGT AAT CCT TAC ATG ATC GTA TTT GGT GTG<br>Asp Pro Cys His Met Ser Ser Asn Pro Tyr Met Ile Val Phe Gly Val<br>    175     180     185 | 640 |
| GCA GAG ATC TTG CTC TCT CAG GTT CCT GAT TTC GAT CAG ATT TGG TGG<br>Ala Glu Ile Leu Leu Ser Gln Val Pro Asp Phe Asp Gln Ile Trp Trp<br>    190     195     200 | 688 |
| ATC TCC ATT GTT GCA GCT GTT ATG TCC TTC ACT TAC TCT GCC ATT GGT<br>Ile Ser Ile Val Ala Ala Val Met Ser Phe Thr Tyr Ser Ala Ile Gly<br>205     210     215 | 736 |
| CTA GCT CTT GGA ATC GTT CAA GTT GCA GCG AAT GGA GTT TTC AAA GGA<br>Leu Ala Leu Gly Ile Val Gln Val Ala Ala Asn Gly Val Phe Lys Gly<br>220     225     230     235 | 784 |
| AGT CTC ACT GGA ATA AGC ATC GGA ACA GTG ACT CAA ACA CAG AAG ATA<br>Ser Leu Thr Gly Ile Ser Ile Gly Thr Val Thr Gln Thr Gln Lys Ile<br>    240     245     250 | 832 |
| TGG AGA ACC TTC CAA GCA CTT GGA GAC ATT GCC TTT GCG TAC TCA TAC<br>Trp Arg Thr Phe Gln Ala Leu Gly Asp Ile Ala Phe Ala Tyr Ser Tyr<br>    255     260     265 | 880 |
| TCT GTT GTC CTA ATC GAG ATT CAG GAT ACT GTA AGA TCC CCA CCG GCG<br>Ser Val Val Leu Ile Glu Ile Gln Asp Thr Val Arg Ser Pro Pro Ala<br>    270     275     280 | 928 |
| GAA TCG AAA ACG ATG AAG AAA GCA ACA AAA ATC AGT ATT GCC GTC ACA<br>Glu Ser Lys Thr Met Lys Lys Ala Thr Lys Ile Ser Ile Ala Val Thr<br>285     290     295 | 976 |
| ACT ATC TTC TAC ATG CTA TGT GGC TCA ATG GGT TAT GCC GCT TTT GGA<br>Thr Ile Phe Tyr Met Leu Cys Gly Ser Met Gly Tyr Ala Ala Phe Gly<br>300     305     310     315 | 1024 |
| GAT GCA GCA CCG GGA AAC CTC CTC ACC GGT TTT GGA TTC TAC AAC CCG<br>Asp Ala Ala Pro Gly Asn Leu Leu Thr Gly Phe Gly Phe Tyr Asn Pro<br>    320     325     330 | 1072 |
| TTT TGG CTC CTT GAC ATA GCT AAC GCC GCC ATT GTT GTC CAC CTC GTT<br>Phe Trp Leu Leu Asp Ile Ala Asn Ala Ala Ile Val Val His Leu Val<br>    335     340     345 | 1120 |

```
GGA GCT TAC CAA GTC TTT GCT CAG CCC ATC TTT GCC TTT ATT GAA AAA      1168
Gly Ala Tyr Gln Val Phe Ala Gln Pro Ile Phe Ala Phe Ile Glu Lys
        350                 355                 360

TCA GTC GCA GAG AGA TAT CCA GAC AAT GAC TTC CTC AGC AAG GAA TTT      1216
Ser Val Ala Glu Arg Tyr Pro Asp Asn Asp Phe Leu Ser Lys Glu Phe
365                 370                 375

GAA ATC AGA ATC CCC GGA TTT AAG TCT CCT TAC AAA GTA AAC GTT TTC      1264
Glu Ile Arg Ile Pro Gly Phe Lys Ser Pro Tyr Lys Val Asn Val Phe
380                 385                 390                 395

AGG ATG GTT TAC AGG AGT GGC TTT GTC GTT ACA ACC ACC GTG ATA TCG      1312
Arg Met Val Tyr Arg Ser Gly Phe Val Val Thr Thr Thr Val Ile Ser
            400                 405                 410

ATG CTG ATG CCG TTT TTT AAC GAC GTG GTC GGG ATC TTA GGG GCG TTA      1360
Met Leu Met Pro Phe Phe Asn Asp Val Val Gly Ile Leu Gly Ala Leu
                415                 420                 425

GGG TTT TGG CCC TTG ACG GTT TAT TTT CCG GTG GAG ATG TAT ATT AAG      1408
Gly Phe Trp Pro Leu Thr Val Tyr Phe Pro Val Glu Met Tyr Ile Lys
            430                 435                 440

CAG AGG AAG GTT GAG AAA TGG AGC ACG AGA TGG GTG TGT TTA CAG ATG      1456
Gln Arg Lys Val Glu Lys Trp Ser Thr Arg Trp Val Cys Leu Gln Met
445                 450                 455

CTT AGT GTT GCT TGT CTT GTG ATC TCG GTG GTC GCC GGG GTT GGA TCA      1504
Leu Ser Val Ala Cys Leu Val Ile Ser Val Val Ala Gly Val Gly Ser
460                 465                 470                 475

ATC GCC GGA GTG ATG CTT GAT CTT AAG GTC TAT AAG CCA TTC AAG TCT      1552
Ile Ala Gly Val Met Leu Asp Leu Lys Val Tyr Lys Pro Phe Lys Ser
                480                 485                 490

ACA TAT TGATGATTAT GGACCATGAA CAACAGAGAG AGTGGTGTG TAAAGTTTAC        1608
Thr Tyr
CATTTCAAAG AAAACTCCAA AAATGTGTAT ATTGTATGTT GTTCTCATTT CGTATGGT      1668

CATCTTTGTA ATAAAATTTA AAACTTATGT TATAAATTAT AAAAAAAAAA AAAAAAA       1728

AAAAAAAAAA AA                                                        1740

(2) INFORMATION FOR SEQ ID NO: 4:

(i) SEQUENCE CHARACTERISTICS:
        (A) LENGTH: 493 amino acids
        (B) TYPE: amino acid
        (D) TOPOLOGY: linear (ii) MOLECULE TYPE: protein (xi) SEQUENCE DESCRIPTION: SEQ ID NO: 4:

Met Gly Glu Thr Ala Ala Ala Asn Asn His Arg His His His His
1               5                   10                  15

Gly His Gln Val Phe Asp Val Ala Ser His Asp Phe Val Pro Pro Gln
                20                  25                  30

Pro Ala Phe Lys Cys Phe Asp Asp Gly Arg Leu Lys Arg Thr Gly
            35                  40                  45

Thr Val Trp Thr Ala Ser Ala His Ile Ile Thr Ala Val Ile Gly Ser
    50                  55                  60

Gly Val Leu Ser Leu Ala Trp Ala Ile Ala Gln Leu Gly Trp Ile Ala
65                  70                  75                  80

Gly Pro Ala Val Met Leu Leu Phe Ser Leu Val Thr Leu Tyr Ser Ser
                85                  90                  95

Thr Leu Leu Ser Asp Cys Tyr Arg Thr Gly Asp Ala Val Ser Gly Lys
            100                 105                 110

Arg Asn Tyr Thr Tyr Met Asp Ala Val Arg Ser Ile Leu Gly Gly Phe
```

-continued

```
            115                 120                 125
Lys Phe Lys Ile Cys Gly Leu Ile Gln Tyr Leu Asn Leu Phe Gly Ile
        130                 135                 140
Ala Ile Gly Tyr Thr Ile Ala Ala Ser Ile Ser Met Met Ala Ile Lys
145                 150                 155                 160
Arg Ser Asn Cys Phe His Lys Ser Gly Gly Lys Asp Pro Cys His Met
                165                 170                 175
Ser Ser Asn Pro Tyr Met Ile Val Phe Gly Val Ala Glu Ile Leu Leu
                180                 185                 190
Ser Gln Val Pro Asp Phe Asp Gln Ile Trp Trp Ile Ser Ile Val Ala
        195                 200                 205
Ala Val Met Ser Phe Thr Tyr Ser Ala Ile Gly Leu Ala Leu Gly Ile
210                 215                 220
Val Gln Val Ala Ala Asn Gly Val Phe Lys Gly Ser Leu Thr Gly Ile
225                 230                 235                 240
Ser Ile Gly Thr Val Thr Gln Thr Gln Lys Ile Trp Arg Thr Phe Gln
                245                 250                 255
Ala Leu Gly Asp Ile Ala Phe Ala Tyr Ser Tyr Ser Val Val Leu Ile
                260                 265                 270
Glu Ile Gln Asp Thr Val Arg Ser Pro Pro Ala Glu Ser Lys Thr Met
        275                 280                 285
Lys Lys Ala Thr Lys Ile Ser Ile Ala Val Thr Thr Ile Phe Tyr Met
        290                 295                 300
Leu Cys Gly Ser Met Gly Tyr Ala Ala Phe Gly Asp Ala Ala Pro Gly
305                 310                 315                 320
Asn Leu Leu Thr Gly Phe Gly Phe Tyr Asn Pro Phe Trp Leu Leu Asp
                325                 330                 335
Ile Ala Asn Ala Ala Ile Val Val His Leu Val Gly Ala Tyr Gln Val
                340                 345                 350
Phe Ala Gln Pro Ile Phe Ala Phe Ile Glu Lys Ser Val Ala Glu Arg
        355                 360                 365
Tyr Pro Asp Asn Asp Phe Leu Ser Lys Glu Phe Glu Ile Arg Ile Pro
        370                 375                 380
Gly Phe Lys Ser Pro Tyr Lys Val Asn Val Phe Arg Met Val Tyr Arg
385                 390                 395                 400
Ser Gly Phe Val Val Thr Thr Val Ile Ser Met Leu Met Pro Phe
                405                 410                 415
Phe Asn Asp Val Val Gly Ile Leu Gly Ala Leu Gly Phe Trp Pro Leu
                420                 425                 430
Thr Val Tyr Phe Pro Val Glu Met Tyr Ile Lys Gln Arg Lys Val Glu
                435                 440                 445
Lys Trp Ser Thr Arg Trp Val Cys Leu Gln Met Leu Ser Val Ala Cys
        450                 455                 460
Leu Val Ile Ser Val Val Ala Gly Val Gly Ser Ile Ala Gly Val Met
465                 470                 475                 480
Leu Asp Leu Lys Val Tyr Lys Pro Phe Lys Ser Thr Tyr
                485                 490
```

SMALL AND CYSTEINE RICH ANTIFUNGAL DEFENSIN AND THIONIN-LIKE PROTEIN GENES HIGHLY EXPRESSED IN THE INCOMPATIBLE INTERACTION

This is a division of application Ser. No. 09/442,631 filed Nov. 18, 1999, now U.S. Pat. No. 6,300,489.

BACKGROUND OF THE INVENTION

The present invention related to two cDNA clones, designated to PepDef (pepper defensin protein gene) and PepThi (pepper thionin-like protein gene) and individual component; thereof including its coding region and its gene product; modification thereto; application of said gene, coding region and modification thereto; DNA construct, vectors and transformed plants each comprising the gene or part thereof.

Plants have developed defense mechanisms to defend themselves against phytopathogens. Plants' first responses to pathogen infection include fortification of cell walls for physical barriers by deposition of lignin (Dean and Kuc, 1988) and by oxidative cross-linking (Brisson et al., 1994) as well as the hypersensitive reaction (HR). HR causes a rapid cell death of infected tissues to halt further colonization by pathogens (Goodman and Novacky, 1994). The next array of defense strategies includes the production of antimicrobial phytoalexins (van Etten et al., 1989), pathogenesis-related (PR) proteins (Linthorst, 1991; Ponstein et al., 1994), and cysteine (Cys)-rich proteins, such as lipid transfer protein (Garcia-Olmedo et al., 1995) and thionins (Bohlmann, 1994).

Thionins are small, highly basic, Cys-rich proteins that show antimicrobial activity and seem to have a role in plant defense against fungi and bacteria. The overexpression of the THI2.1 thionin in Arabidopsis enhanced resistance to a phytopathogenic fungus (Epple et al., 1997). The overexpression of α-hordothionin in tobacco also enhanced resistance to a phytopathogenic bacterium (Carmona et al., 1993). In addition, during barley and powdery mildew interactions, the accumulation of thionins was higher in the incompatible interaction than in the compatible one (Ebrahim-Nesbat et al., 1993).

The thionins contain a signal sequence, the thionin domain and an acid polypeptide domain as well as the conserved Cys residues (Bohlmann et al., 1994). A new class of Cys-rich antimicrobial protein, γ-thionin, has a similar size (5 kD) and the same number of disulfide bridges as thionins. However, since γ-thionins do not have significant sequence homologies with thionins, they have been described as plant defensins (Terras et al., 1995). Both defensin and thionin genes in Arabidopsis are inducible via a salicylic acid-independent pathway different from that for PR proteins (Epple et al., 1995; Penninckx et al., 1996).

Fruit ripening represents a genetically synchronized process that involves developmental events unique to plant species. Generally, ripe fruits are susceptible to pathogen attack (Swinburne, 1983; Prusky et al., 1991). Therefore, fruit as one of the reproductive organs of the plants must be protected from pathogens to maintain their integrity and seed maturation. Several antifungal proteins that are responsible for protection against pathogens during fruit ripening have been identified (Fils-Lycaon et al., 1996; Meyer et al., 1996; Salzman et al., 1998). Also, PR proteins are developmentally expressed during the formation of flowers (Lotan et al., 1989; Cote et al., 1991).

*Colletotrichum gloeosporioides* (Penz.) causes anthracnose diseases in many plant species (Daykin, 1984; Dodds et al., 1991; Prusky et al., 1991). *C. gloeosporioides* is the most prevalent species among *C. acutatum, C. coccodes, C. dematium, C. gloeosporioides,* and *G. cingulata* to cause anthracnose diseases on pepper (*Capsicum annuum* L.) (Kim et al., 1986; Manandhar et al., 1995). In previous study, we found that the unripe-mature-green fruit of pepper cv. Nokkwang interacted compatibly with *C. gloeosporioides*, whereas the interaction of the ripe-red fruits with fungus was incompatible (Oh et al., 1998). To investigate the activation of defense-related genes from the incompatible-pepper fruit upon *C. gloeosporioides* infection, we isolated a defensin gene and a thionin-like gene by using mRNA differential display. The regulation of these Cys-rich protein genes was studied during fruit ripening and in the initial infection process during the compatible and incompatible interactions. We report here what appears to be the first case of a defensin gene and a thionin-like gene induced via different signal transduction pathways in a plant and fungus interaction.

SUMMARY OF THE INVENTION

The present invention relates to two cDNA clones, designated to a defensin gene, PepDef, and a thionin-like gene, PepThi, the sequences of which are depicted in SEQ ID No. 3 and No. 1, respectively. The anthracnose fungus, *C. gloeosporioides*, interacts incompatibly with ripe fruits of pepper (*Capsicum annuum*). It interacts compatibly with the unripe-mature fruits. We isolated PepDef and PepThi expressed in the incompatible interaction by using mRNA differential display method. Both genes were developmentally regulated during fruit ripening, organ-specifically regulated, and differentially induced during the compatible and incompatible interactions. The expression of PepThi gene was rapidly induced in the incompatible-ripe fruit upon fungal infection. The fungal-inducible PepThi gene is highly inducible only in the unripe fruit by salicylic acid. In both ripe and unripe fruits, it was induced by wounding, but not by jasmonic acid. The expression of PepDef gene is enhanced in the unripe fruit by jasmonic acid, while suppressed in the ripe fruit. These results suggest that both small and cysteine-rich protein genes are induced via different signal transduction pathways during fruit ripening to protect the reproductive organs against biotic and abiotic stresses. The PepDef and PepThi car be cloned into an expression vector to produce a recombinant DNA expression system suitable for insertion into cells to form a transgenic plant transformed with these genes. In addition, the PepDef and PepThi genes of this invention can be also used to produce transgenic plants that exhibit enhanced resistance against phytopathogens, including fungi, bacteria, viruses, nematode, mycoplasmalike organisms, parasitic higher plants, flagellate protozoa, and insects.

BRIEF DESCRIPTION OF THE DRAWINGS

FIG. 1. Alignment of the deduced amino acid sequences from PepDef (GenBank accession number X95363) and PepThi cDNAs (AF112443) of pepper (Meyer et al., 1996) with other thionins from tomato (*Lycopersicon esculentum,* U20591; Milligan and Gasser, 1995), *Nicotiana excelsior* (AB005266), tobacco (*N. tabacum,* Z 11748; Gu et al., 1992), and *N. paniculata* (AB005250). The conserved cysteine arrangement —C( . . . )C—X—X—X—C( . . . )G-X—C( . . . )C—X—C— is indicated by arrows.

DETAILED DESCRIPTION OF THE INVENTION

Figure 2:
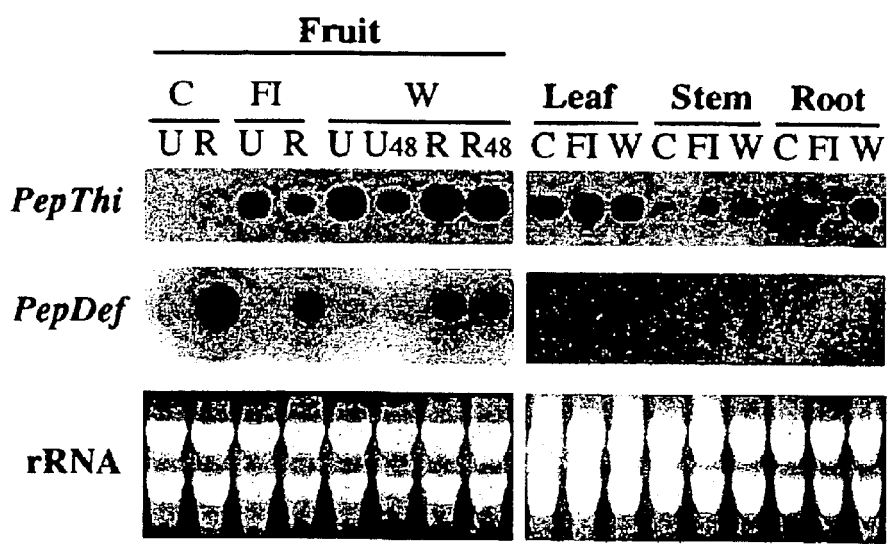
FIG. 2. Expression and induction of PepDef and PepThi genes from various organs of pepper by *Colletotrichum gloeosporioides* infections and wounding. RNAs were isolated from ripe fruit (R), unripe fruit (U), leaf, stem, and root at 24 h after the treatments of fungal infection (FI) and wounding (W). In addition, RNAs of both ripe and unripe fruits at 48 h after wounding (R48 and U48) were isolated. Ten µl at $5 \times 10^5$ conidialml of *C. gloeosporioides* was used for the inoculation of various pepper organs. Organs treated with 10 µl sterile-water except fungal spores for 24 h were used as the controls (C).

The present invention has identified two cDNA clones, designated to PepDef and PepThi, from the incompatible interaction between pepper and the pepper anthracnose fungus *Colletotrichum gloeosporioides* using MRNA differential display and cDNA library screening.

Figure 1:
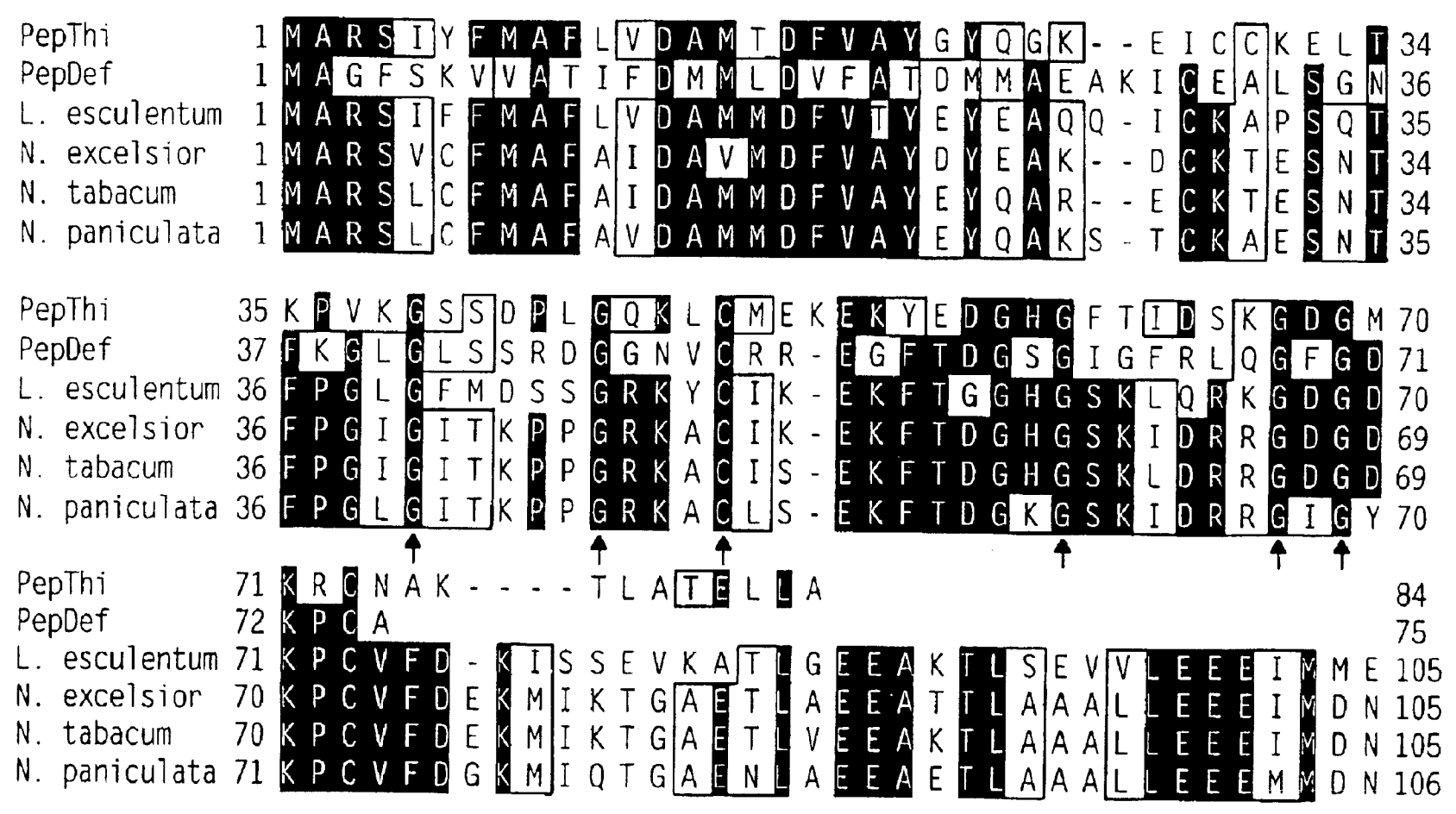

The PepThi cDNA is 506 bp in length with 9 bp of 5'-untranslated region and 245 bp of 3'-untranslated region including the poly(A) tail (GenBank AF 112443). The PepThi clone represented a full-length cDNA of the 0.5 kb transcript identified by RNA gel blot analysis. The cDNA contained one open reading frame encoding a polypeptide of 9.5 kDa with 84 amino acids. The deduced amino acid sequence of PepThi (SEQ ID No. 2) contained an N-terminal secretory signal peptide that was cleaved after glycine at position 25 (FIG. 1). PepThi is a Cys-rich polypeptide containing the consensus Cys arrangement —C( . . . ) C—X—X—X—C( . . . )G-X—C( . . . )C—X—C—.

The PepDef cDNA is 225 bp except 5'-untranslated region and 3'-untranslated region including the poly(A) tail (X95363). The PepDef clone represented a full-length DNA of the 0.45 kb transcript identified by RNA gel blot analysis. The cDNA contained one open reading frame encoding a polypeptide of 8.5 kDa with 75 amino acids. The deduced amino acid sequence of PepDef(SEQ ID No. 4) contained an N-terminal secretory signal peptide that was cleaved after alanine at position 27 (FIG. 1). PepDef is also a Cys-rich polypeptide containing the consensus Cys arrangement —C( . . . )C—X—X—X—C( . . . )G-X—C( . . . )C—X—C—.

The expression of PepThi gene was observed in ripe fruits, leaves, stems, and roots of pepper, respectively. The basal and non-induced level of PepThi gene was higher in the leaves and roots than in the fruits and stems. In the fruits, the PepThi mRNA was highly induced by fungal infection and wounding. Also, the accumulation of the PepThi mRNA increased in the stems with fungal infection and wounding. However, the level of PepThi mRNA was not significantly changed in the leaves and roots by the treatments.

The PepDef mRNA was not detected in leaves, stems, and roots even after fungal infection and wounding. However, the basal level of PepDef gene was very high in the ripe fruit, and undetectably low in the unripe fruit. Interestingly, the level of PepDef mRNA was reduced in the ripe fruit by fungal infection and wounding. This phenomenon was also observed in the ripe fruit by JA treatment. The accumulation of PepDef mRNA was not significantly induced in the unripe fruit by fungal infection and wounding for 24 h or 48 h. These results suggest that PepDef and PepThi genes are developmentally and organ-specifically regulated, and the induction by fungal infection and wounding is also subject to developmental regulation.

To examine the time course of the induction of PepDef or PepThi mRNAs in response to the fungal infection, RNA gel blot analysis was performed with the ripe and unripe fruits at 0, 3, 6, 12, 24, 48, and 72 h after inoculation (HAI) using PepDef and PepThi cDNAs as probes. The uninoculated incompatible-ripe fruit contained a basal level of PepThi mRNA. However, the expression of PepThi was rapidly induced in the ripe fruit upon fungal infection and reached a maximum at 48 and 72 HAIs. In compatible-unripe fruits, the accumulation of PepThi mRNA was late, at 12 HAI, and reached its maximum level at 72 HAI.

Accumulation of PepDef mRNA in the unripe fruit was very low. PepDef expression was suppressed by fungal infection in the ripe fruit. The transcript levels dropped until 48 HAI, and had begun to increase again 72 HAI. Since PepDef gene was highly expressed in the ripe fruit and PepThi gene was induced in the ripe fruit by the fungal infection, these genes may be involved in the defense mechanism during fruit ripening against the phytopathogen.

Figure 4:
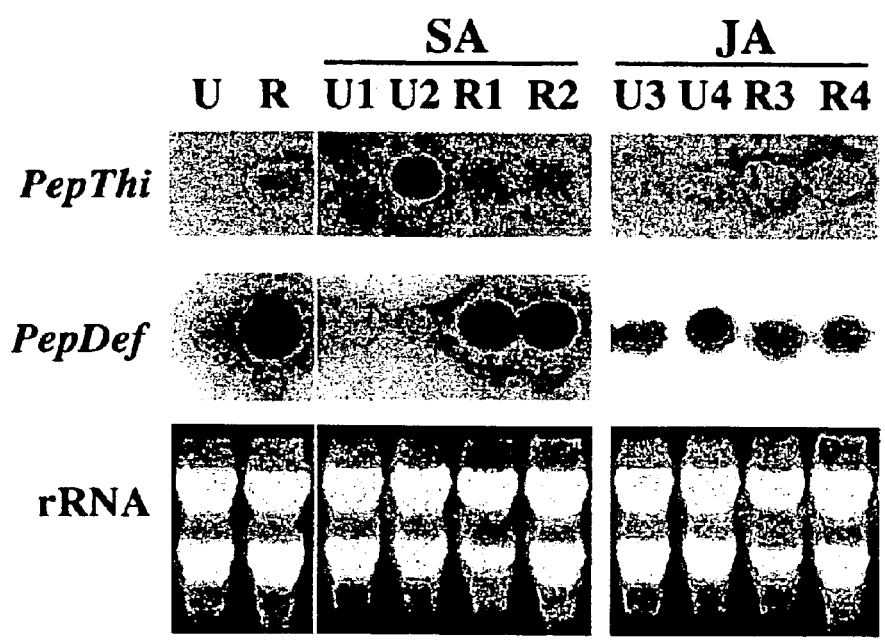
FIG. 4. Induction and suppression of PepDef and PepThi genes from both ripe and unripe fruits of pepper by exogenous salicylic acid (SA) and jasmonic acid (JA) treatments. RNAs were isolated from both ripe (R) and unripe fruits (U) treated with SA (1=0.5 mM, 2=5 mM) and JA (3=4 µM, 4=40 µM) for 24 h. Fruits treated with 10 µl sterile-water except fungal spores for 24 h were used as the control (C).

To identify inducers of PepDef and PepThi gene expression from fruits, RNA gel blot analysis was performed with unripe and ripe fruits treated with exogenous jasmonic acid (JA) and salicylic acid (SA) for 24 h. The PepThi mRNA was highly accumulated in the unripe fruit compared to in the ripe fruit by SA at 5 MM (FIG. 4). However, JA could not significantly induce the PepThi mRNA in both ripe and unripe fruits. The expression level of PepDef mRNA was not changed in both ripe and unripe fruits by SA. Interestingly, the expression of PepDef mRNA by JA increased in the unripe fruit, but decreased slightly in the ripe fruit. Taken together, these results suggest that the PepThi and PepDef genes are expressed via different signal transduction pathways during ripening.

The PepDef and PepThi genes can be cloned into an expression vector to produce a recombinant DNA expression system suitable for insertion into cells to form a transgenic plant transformed with these genes. In addition, the PepDef and PepThi genes of this invention can be also used to produce transgenic plants that exhibit enhanced resistance against phytopathogens, including fungi, bacteria, viruses, nematode, mycoplasmalike organisms, parasitic higher plants, flagellate protozoa, and insects.

EXAMPLES

Fungal Inoculum and Plant Material

Monoconidial isolate KG13 of *C. gloeosporioides* was cultured on potato dextrose agar (Difco, USA) for 5 days in darkness at 27° C. Sterile distilled water was added and conidia were harvested through four layers of cheesecloth to remove mycelial debris. Ten µl at $5 \times 10^5$ conidia/ml of *C. gloeosporioides* was used for the inoculation of both unripe and ripe pepper fruit as described (Oh et al., 1998).

Both ripe-red and unripe-mature-green fruits of pepper cv. Nokkwang were grown and harvested under green-house conditions. For wound treatments, five healthy ripe and unripe fruits were deeply scratched by a knife and incubated under relative humidity of 100% at 27° C. in the dark. Ten µl of SA (0.5 and 5 mM) and JA (4 and 40 µM) was applied to both ripe and unripe sets of five fruits. After incubation under the condition described above, the fruits were excised to 1 cm² at the application site and frozen in liquid nitrogen. Leaf, root, and stem samples were harvested from 3-week-old plants and handled as described above for fungal inoculation and wounding.

mRNA Differential Display

Total RNA was extracted from healthy and infected ripe and unripe fruits using RNeasy Plant kit (Qiagen, Germany) according to the manufacturer's instruction. We used total RNA as template for the reverse transcriptase reaction and performed differential display with [$\alpha^{33}$P]dATP instead of [$\alpha^{35}$S]dATP (Liang and Pardee, 1992). Anchored primers and random-arbitrary primers were purchased from Operon Technologies (Alameda, Calif., USA). PCR-amplified cDNA fragments were separated on denaturing 5% polyacrylamide gels in Tris-borate buffer. cDNAs were recovered from the gel, amplified by PCR, and cloned into pGEM-T easy vector (Promega, USA) as described (Oh et al., 1995).

Construction and Screening of cDNA Library

Poly(A)$^+$ mRNA was purified from total RNA of unripe fruits at 24 and 48 h after inoculation with C. gloeosporioides using Oligotex mRNA Kit (Qiagen, Germany). The cDNA library (2.5×10$^5$ plaque-forming unit with the mean insert size of 1.2 kb) was constructed in the cloning vector XZAPII (Stratagene, Germany) according to the manufacturer's instruction.

A partial cDNA, designated pddThi, from the differential display was used as a probe to screen the C. gloeosporioides-induced pepper cDNA library. After three rounds of plaque hybridization, positive plaques were purified. The pBluescript SK phagemid containing cDNAs was excised in vivo from the ZAP Express vector using the ExAssit helper phage.

DNA Sequencing and Homology Search

The cDNA sequencing was performed with an ALFexpress automated DNA sequencer (Pharmacia, Sweden). Analysis of nucleotide and amino acid sequences was performed using the DNASIS sequence analysis software for Windows, version 2.1 (Hitachi, Japan). The multiple sequence alignment was produced with the Clustal W program. For a homology search, cDNA sequence was compared to the NCBI non-redundant databases using the BLAST electronic mail server (Altschul et al., 1997).

RNA Blot and Hybridization

Total RNA (10 µg/lane) from each plant tissue used in this study was separated on 1.2% denaturing agarose gels in the presence of formaldehyde. RNA gel-blotting, hybridization and washing were conducted as described by the manufacturer of the positively charged nylon membrane employed (Hybond N$^+$; Amersham, UK). Radiolabeled probes were prepared with [$\alpha^{32}$P]dCTP (Amersham) using a random primer-labeling kit (Boehringer Mannheim, Germany).

Cloning and Characterization of Thionin-Like cDNAs

C. gloeosporioides showed the incompatible interaction with ripe-red fruits of pepper and the compatible interaction with unripe-mature-green fruits (Oh et al., 1998). We isolated several cDNAs induced from the ripe fruit, but not from the unripe fruit by the fungal infection using mRNA differential display. By nucleotide sequence analysis of cDNAs, two cDNA fragments were identified to be thionin homologs. One cDNA was full length and was similar to j1-1 cDNA that encodes a fruit specific defensin (Meyer et al., 1996). We named the defensin as PepDef (pepper defensin). Another cDNA fragment, designated pddThi, showed homology to γ-thionin from tobacco (Gu et al., 1992). In preliminary RNA gel blot analysis, the two mRNAs accumulated to high levels in the incompatible interaction. A full-length cDNA clone of pddThi was isolated from a cDNA library prepared from pepper fruits 24 and 48 h after inoculation with the fungus. The full-length clone was designated pPepThi (pepper thionin) and sequenced.

The pPepThi cDNA is 506 bp in length with 9 bp of 5'-untranslated region and 245 bp of 3'-untranslated region including the poly(A) tail (GenBank AF112443). The pPepThi clone represented a full-length cDNA of the 0.5 kb transcript identified by RNA gel blot analysis. The cDNA contained one open reading frame encoding a polypeptide of 9.5 kDa with 84 amino acids. The deduced amino acid sequence of PepThi contained an N-terminal secretory signal peptide that was cleaved after glycine at position 25 (FIG. 1). PepThi is a Cys-rich polypeptide containing the consensus Cys arrangement —C( . . . )C—X—X—X—C ( . . . )G-X—C( . . . )C—X—C—.

A sequence alignment showed that the PepThi shared significant homology (identity and similarity: 50% and 64%, respectively) to a flower-specific γ-thionin from tobacco (Gu et al., 1992) and to several other γ-thionins from Nicotiana species and tomato (Milligan and Gasser, 1995; FIG. 1). PepThi protein showed 29% identity for the whole coding region to a pepper defensin protein PepDef. PepThi did not have nucleotide sequence homology to thionins and was different from other γ-thionins. Thus, we assigned PepThi as a thionin-like protein.

Expression Pattern and Induction by Fungal Infection and Wounding

To examine the PepThi gene expression in various organs and its inducibility by fungal inoculation and wounding, RNA gel blot analysis was performed using total RNAs prepared from fruits, leaves, stems, and roots of pepper plants at 24 h after treatments. The expression of Peplhi gene was observed in ripe fruits, leaves, stems, and roots (FIG. 2). The basal and non-induced level of PepThi gene was higher in the leaves and roots than in the fruits and stems. In the fruits, the PepThi mRNA was highly induced by fungal infection and wounding. Also, the accumulation of the PepThi mRNA increased in the stems with fungal infection and wounding. However, the level of PepThi mRNA was not significantly changed in the leaves and roots by the treatments.

We hybridized the PepDef cDNA to the same blot that was used for the hybridization of PepThi cDNA. The basal level of PepDef gene was very high in the ripe fruit, and undetectably low in the unripe fruit (FIG. 2). The PepDef mRNA was not detected in leaves, stems, and roots even after the treatments. PepDef protein is wound-inducible in the unripe fruit at 3 days after treatment (Meyer et al., 1996). However, the accumulation of PepDef mRNA was not significantly induced in the unripe fruit by fungal infection and wounding for 24 h or 48 h. Interestingly, the level of PepDef mRNA was reduced in the ripe fruit by fungal infection and wounding. These phenomena were also observed in the ripe fruit by fungal infection and JA treatment (see FIGS. 3 and 4). These results suggest that PepThi and PepDef genes are developmentally and organ-specifically regulated, and the induction by fungal infection and wounding is also subject to developmental regulation.

Differential Induction by Fungal Infection During Fruit Ripening

Figure 3:
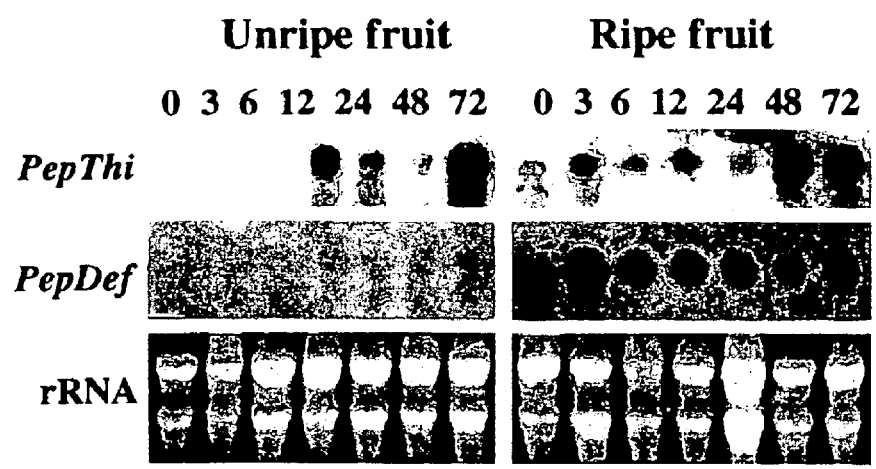
FIG. 3. Differential induction of PepDef and PepThi genes from both ripe and unripe fruits of pepper by *Colletotrichum gloeosporioides* infections. RNAs were isolated from both ripe (incompatible interaction) and unripe fruits (compatible interaction) after the fungal infection with time course. Time is indicated in h after infection.

In our previous study for fungal morphogenesis on the surface of fruits, conidial germination, initial and mature infection hypha were observed at 2, 12, and 24 h after inoculations (HAIs), respectively (Oh et al. 1998). The initial anthracnose symptoms were detected only on the unripe fruit at 2 days after inoculation, resulting in typical sunken necrosis within 5 days after inoculation. To examine the time course of the induction of PepThi or PepDef mRNAs in response to the fungal infection, RNA gel blot analysis was performed with the ripe and unripe fruits at 0, 3, 6, 12, 24, 48, and 72 HAI using PepThi and j1-1 cDNAs as probes. The uninoculated incompatible-ripe fruit contained a basal level of PepThi mRNA (FIGS. 2 and 3). However, the expression of PepThi was rapidly induced in the ripe fruit upon fungal infection and reached a maximum at 48 and 72 HAIs (FIG. 3). In compatible-unripe fruits, the accumulation of PepThi mRNA was late, at 12 HAI, and reached its maximum level at 72 HAI.

Accumulation of PepDef mRNA in the unripe fruit was very low (FIG. 3). As shown in FIG. 2, PepDef expression was suppressed by fungal infection in the ripe fruit. The transcript levels dropped until 48 HAI, and had begun to increase again 72 HAI. Since PepDef gene was highly expressed in the ripe fruit and PepThi gene was induced in the ripe fruit by the fungal infection, these genes may be involved in the defense mechanism during fruit ripening against the phytopathogen.

Induction and Suppression During Fruit Ripening by JA and SA

To identify the inducers of PepThi and PepDef gene expression from fruits, RNA gel blot analysis was performed with the unripe and ripe fruits treated with exogenous JA and SA for 24 h. The PepThi mRNA was highly accumulated in the unripe fruit compared to in the ripe fruit by SA at 5 mM (FIG. 4). However, JA could not significantly induce the PepThi mRNA in both ripe and unripe fruits. The expression level of PepDef mRNA was not changed in both ripe and unripe fruits by SA. Interestingly, the expression of PepDef mRNA by JA increased in the unripe fruit, but decreased slightly in the ripe fruit. Taken together, these results suggest that the PepThi and PepDef genes are expressed via different signal transduction pathways during ripening.

Discussion

Fungal-inducible thionin genes were identified in several plant/fungus interactions, such as in *Arabidopsis/Fusarium oxysporum* f.sp. *matthiolae* (Epple et al., 1995), barley/ *Stagonospora nodorum* (Titarenko et al., 1993; Stevens et al., 1996), and barley/the mildew fungus (Boyd et al., 1994; Bohlmann et al., 1998). Relevant to these findings, the accumulation of barley leaf thionin in papillae and in the cell wall surrounding the infection peg was higher in the incompatible interaction than that in the compatible one (Ebrahim-Nesbat et al., 1989, 1993). Similar phenomena have been reported for many other plant and pathogen interactions. The induction of PepThi mRNA was observed to be faster in the incompatible interaction of ripe pepper fruits with the fungus (FIG. 3).

The PepThi gene was induced during the early conidial germination of the fungus, before infection hyphae formation (Oh et al., 1998) and even before appressorium formation (Kim et al., 1999). These results suggest that signaling compounds released/produced during fungal germination result in the expression of PepThi gene in the epidermal cells of the incompatible-ripe fruit. Since the PepThi gene is expressed in various organs of pepper plants and its expression level is enhanced by fungal inoculation and wounding (FIG. 2), PepThi thionin-like protein could play a role in conferring systemic protection for the plants against both biotic and abiotic stresses. Also, the induction of PepThi gene in the unripe fruit by SA (FIG. 4) is consistent with a systemic protection role. SA plays an important role in the signal transduction pathway leading to the systemic acquired resistance (Gaffney et al., 1993).

The expression of the PepDef gene is regulated during fruit ripening. Similarly, several defensins and thionins are specifically expressed in reproductive organs, such as flowers in tobacco (Gu et al., 1992) and Arabidopsis (Epple et al., 1995), pistils in petunia (Karunanandaa et al., 1994), and seeds in radish (Terras et al., 1995). These findings suggest that both defensins and thionins are possibly involved in the defense mechanism for protecting the reproductive organ against pathogens or wounds. Further, thionins and other Cys-rich proteins exhibit synergistically enhanced antifungal activity (Terras et al., 1993). Therefore, the concerted expression of both PepDef and PepThi genes during ripening could confer disease resistance in the ripe fruit during the early fungal infection process.

The responses to exogenous JA and SA treatments in pepper during fruit ripening are different for both PepDef and PepThi genes. JA as a chemical elicitor induces thionin genes in Arabidopsis (Epple et al., 1995; Vignutelli et al., 1998) and barley (Andresen et al., 1992), and defensin genes in Arabidopsis (Penninckx et al., 1996), in addition to other wound inducible genes (Hildmann et al., 1992; Reinbothe et al., 1994). SA also induces a thionin gene in barley leaf (Kogel et al., 1995) as well as PR proteins (Ward et al., 1991; Uknes et al., 1992). A JA-independent wound induction pathway that shows opposite regulation to the JA-dependent one was identified in Arabidopsis (Rojo et al., 1998). In the present study, the PepThi gene is strongly inducible in the unripe fruit by SA and wounding, but not by JA (FIG. 4). These data indicate that the PepThi gene is expressed via a JA-independent wound signal transduction pathway.

Since the PepDef gene is induced in the unripe fruit by JA, it is probably regulated via the octadecanoid pathway (Peña-Cortés et al., 1995; Bergey et al., 1996). The slightly suppression of the PepDef gene in the ripe fruit by JA and wounding is puzzling, since both JA in the unripe fruit result in the induction of PepDef RNA. The possible explanation is that JA may elicit other signals that are able to activate genes in response to JA. These additional signals may result in the inhibition of PepDef expression in the ripe fruit.

This present study shows that a defensin and a thionin-like protein that may have defensive roles are deployed via different signal transduction pathways and may protect pepper fruits against the anthracnose fungus.

REFERENCES

1. Altschul S F, Madden T L, Schäffer A A, Zhang J, Zhang Z, Miller W, Lipman D J: Gapped BLAST and PSI-BLAST: a new generation of protein database search programs. Nucleic Acids Res 25: 3389–3402 (1997).
2. Andresen I, Becker W, Schlüter K, Burges J, Parthier B, Apel K: The identification of leaf thionin as one of the main jasmonate-induced proteins of barley (*Hordeum vulgare*). Plant Mol Biol 19: 193–204 (1992).
3. Bergey D R, Howe G A, Ryan C A: Polypeptide signaling for plant defensive genes exhibits analogies to defense signaling in animals. Proc Natl Acad Sci USA 93: 12053–12058 (1996).
4. Bohlmann H: The role of thionins in plant protection. Crit Rev Plant Sci 13: 1–16 (1994).
5. Bohlmann H, Apel K, Garcia-Olmedo F: Thionins. Plant Mol Biol Rep 12: S75 (1994).
6. Bohlmann H, Clausen S, Behnke S, Giese H, Hiller C, Schrader G, Barkholt V, Apel K: Leaf-thionins of barley—a novel class of cell wall proteins toxic to plant-pathogenic fungi and possibly involved in the defense mechanism of plants. EMBO J 7: 1559–1565 (1988).
7. Brisson L F, Tenhaken R, Lamb C: Functions of oxidative cross-linking of cell wall structural proteins in plant disease resistance. Plant Cell 6: 1703–1712 (1994).
8. Boyd L A, Smith P H, Green R M, Brown J K M: The relationship between the expression of defense-related genes and mildew development in barley. Mol Plant-Microbe Interact 7: 401–410 (1994).

9. Carmona M J, Molina A, Fernandez J A, Lopez-Fando J J, Garcia-Olmedo F: Expression of the α-thionin gene from barley in tobacco confers enhanced resistance to bacterial pathogens. Plant J 3: 457–462 (1993).
10. Coté F, Cutt J R, Asselin A, Klessig D F: Pathogenesis-related acidic β-1,3-glucanase genes of tobacco are regulated by both stress and developmental signals. Mol Plant-Microbe Interact 4: 173–181 (1991).
11. Daykin M E: Infection in blueberry fruit by *Colletotrichum gloeosporioides*. Plant Dis 68: 984–950 (1984).
12. Dean R A, Kúc J: Rapid lignification in response to wounding and infection as a mechanism for induced systemic protection in cucumber. Physiol Plant Pathol 31: 69–81 (1988).
13. Dodds J C, Estrada A, Matcham A, Jeffries P, Jeger M J: The effect of environmental factors on *Colletotrichum gloeosporioides*, the causal agent of mango anthracnose, in the Philippines. Plant Pathol 40: 568–575 (1991).
14. Ebrahim-Nesbat F, Behnke S, Kleinhofs A, Apel K: Cultivar-related differences in the distribution of cell-wall bound thionins in compatible and incompatible interactions between barley and powdery mildew. Planta 179: 203–210 (1989).
15. Ebrahim-Nesbat F, Bohl S, Heitefuss R, Apel K: Thionin in cell walls and papillae of barley in compatible and incompatible interactions with *Erysiphe graminis* f sp. *hordei*. Physiol Mol Plant Pathol 43: 343–352 (1993).
16. Epple P, Apel K, Bohlmann H: An *Arabidopsis thaliana* thionin gene is inducible via a signal transduction pathway different from that for pathogenesis-related proteins. Plant Physiol 109: 813–820 (1995).
17. Epple P, Apel K, Bohlmann H: Overexpression of an endogenous thionin gives enhanced resistance of Arabidopsis against *Fusarium oxysporum*. Plant Cell 9: 509–520 (1997).
18. Fils-Lycaon B R, Wiersma P A, Eastwell K C, Sautiere P: A cherry protein and its gene, abundantly expressed in ripening fruit, have been identified as thaumatin-like. Plant Physiol 111: 269–273 (1996).
19. Gaffney T, Friedrich L, Vernooij B, Negrotto D, Nye G, Uknes S, Ward E, Kessmann H, Ryals J: Requirement of salicylic acid for the induction of systemic acquired resistance. Science 261: 754–756 (1993).
20. Garcia-Olmedo F, Molina A, Segura A, Moreno M: The defensive role of nonspecific lipid-transfer proteins in plants. Trend Microbiol 3: 72–74 (1995).
21. Goodman R N, Novacky A J: The Hypersensitive Reaction in Plants to Pathogens. A Resistance Phenomenon. APS Press, St. Paul, Minn., USA (1994).
22. Gu Q, Kawarta E F, Mores M-J, Wu H-M, Cheung A Y: A flower specific cDNA encoding a novel thionin in tobacco. Mol Gen Genet 234: 89–96 (1992).
23. Hildmann T, Ebneth M, Peña-Cortés H, Sanches-Serrano J J, Willmitzer L, Prat S: General roles of abscisic acid and jasmonic acids in gene activation as a result of mechanical wounding. Plant Cell 4: 1157–1170 (1992).
24. Karunanandaa B, Singh A, Kao T: Characterization of a predominantly pistil-expressed gene encoding a γ-thionin-like protein of Petunia inflata. Plant Mol Biol 26: 459–464 (1994).
25. Kim W G, Cho E K, Lee E J: Two strains of *Colletotrichum gloeosporioides* Penz. causing anthracnose on pepper fruits. Korean J Plant Pathol 2: 107–113 (1986).
26. Kim K D, Oh B J, Yang J: Differential interactions of a *Colletotrichum gloeosporioides* isolate with green and red pepper fruits. Phytoparasitica 27: 97–106 (1999).
27. Kogel K-H, Ortel B, Jarosch B, Atzom R, Schiffer R, Wastemack C: Resistance in barley against the powdery mildew fungus (*Erysiphe graminis* f.sp. *hordei*) is not associated with enhanced levels of endogenous jasmonates. Eur J Plant Pathol 101: 319–332 (1995).
28. Liang P, Pardee A B: Differential display of eukaryotic messenger RNA by means of the polymerase chain reaction. Science 257: 967–971 (1992).
29. Linthrost H J M: Pathogenesis-related proteins of plants. Crit Rev Plant Sci 10: 123–150 (1991).
30. Lotan T, Ori N, Fluhr R: Pathogenesis-related proteins are developmentally regulated in tobacco flowers. Plant Cell 1: 881–887 (1989).
31. Manandhar J B, Hartman G L, Wang T C: Conidial germination and appressorial formation of *Colletotrichum capsici* and *C. gloeosporioides* isolates from pepper. Plant Dis 79: 361–366 (1995).
32. Meyer B, Houlné G, Pozueta-Romero J, Schantz M-L, Schantz R: Fruit-specific expression of a defensin-type gene family in bell pepper. Upregulation during ripening and upon wounding. Plant Physiol 112: 615–622 (1996).
33. Milligan S B, Gasser C S: Nature and regulation of pistil-expressed gene in tomato. Plant Mol Biol 28: 691–711 (1995).
34. Oh B J, Balint D E, Giovannoni J J: A modified procedure for PCR-based differential display and demonstration of use in plants for isolation of gene related to fruit ripening. Plant Mol Biol rep 13: 70–81 (1995).
35. Oh B J, Kim K D, Kim Y S: A microscopic characterization of the infection of green and red pepper fruits by an isolate of *Colletotrichum gloeosporioides*. J Phytopathol 146: 301–303 (1998).
36. Peña-Cortés H; Fisahn J, Willmitzer L: Signals involves in wound-induced proteinase inhibitor II gene expression in tomato and potato plants. Proc Natl Acad Sci USA 92: 4106–4113 (1995).
37. Penninckx I A, Eggermont K, Terras F R, Thomma B P, De Samblanx G W, Buchala A, Metraux J P, Manners J M, Broekaert W F: Pathogen-induced systemic activation of a plant defensin gene in Arabidopsis follows a salicylic acid-independent pathway. Plant Cell 8: 2309–2323 (1996).
38. Ponstein A S, Bres-Vloemans S A, Sela-Buurlage M B, van den Elzen P J M, Melchers L S, Cornelissen B J C: A novel pathogen- and wound-inducible tobacco (*Nicotiana tabacum*) protein with antifungal activity. Plant Physiol 104: 109–118 (1994).
39. Prusky D, Plumbley R A, Kobiler I: The relationship between the antifungal diene levels and fungal inhibition during quiescent infections of *Colletotrichum gloeosporioides* in unripe avocado fruits. Plant Pathol 40: 45–52 (1991).
40. Reinbothe S, Mollenhauer B, Reinbothe C: JIP and RIPs: the regulation of plant gene expression by jasmonates in response to environmental cues and pathogens. Plant Cell 6: 1197–1209 (1994).
41. Rojo E, Titarenko E, León J, Berger S, Vancanneyt G, Sanchez-Serrano J J: Reversal protein phosphorylation regulates jasmonic acid-dependent and—independent wound signal transduction pathways in *Arabidopsis thaliana*. Plant J 13: 153–165 (1998).
42. Salzman R A, Tikhonova I, Bordelon B P, Hasegawa P M, Bressan R A: Coordinate accumulation of antifungal proteins and hexoses constitutes a developmentally controlled defense response during fruit ripening in grape. Plant Physiol 117: 465–472 (1998).
43. Stevens C, Titarenko E, Hargreaves J A, Gurr S J: Defense-related gene activation during an incompatible interaction between *Stagonospora* (*Septoria*) *nodorum* and barey (*Hordeum vulgare* L.) coleoptile cells. Plant Mol Biol 31: 741–749 (1996).
44. Swinbume T R: Post-Harvest Pathology of Fruits and Vegetables. Academic Press, NY, USA (1983).
45. Terras F R G, Egermont K, Kovaleva V, Raikhel N V, Osborn R W, Kester A, Rees S B, Torrekens S, Van Leuven F, Vanderleyden J, Cammue B P A, Broekaert W F: Small cystein-rich antifungal proteins from radish: their role in host defense. Plant Cell 7: 573–588 (1995).
46. Terras F R G, Schoofs H M E, Thevissen K, Osborn R W, Vanderleyden J, Cammue B P A, Broekaert W F: Synergistic enhancement of the antifungal activity of wheat and barley thionins by radish and oilseed rape 2S albumins and by barley trypsin inhibitors. Plant Physiol 103: 1311–1319 (1993).
47. Titarenko E, Hargreaves J, Keon J, Gurr S J: Defense-related gene expression in barley coleoptile cells following infection by Septoria nodorum. In Mechanisms of Plant Defense responses, Fritig B and Legrand M (eds), pp. 308–311. Kluwer Academic Publisher, Dordrecht (1993).
48. Uknes S, Mauch-Mani B, Moyer M, Potter S, Williams S, Dincher S, Chandler D, Slusarenko A, Ward E, Ryals J: Acquired resistance in Arabidopsis. Plant Cell 4: 645–656 (1992).
49. Van Etten H D, Mattews D E, Mattews P S: Phytoalexin detoxification: Importance for pathogenicity and practical implications. Annu Rev Phytopathol 27:143–164 (1989).
50. Vignutelli A, Wasternack C, Apel K, Bohlmann H: Systemic and local induction of an Arabidopsis thionin gene by wounding and pathogens. Plant J 14: 285–295 (1998).
51. Ward E R, Uknes S J, Williams S C, Dincher S S, Wiederhold D L, Alexander D C, Ahl-Goy P, Metraux J-P, Ryals J A: Coordinate gene activity in response to agents that induce systemic acquired resistance. Plant Cell 3: 1085–1094 (1991).

What is claimed is:

1. An isolated nucleic acid molecule having a nucleic acid sequence of SEQ ID No: 1.

\* \* \* \* \*